US00RE45745E

(19) United States
(12) Reissued Patent
Türker et al.

(10) Patent Number: US RE45,745 E
(45) Date of Reissued Patent: Oct. 13, 2015

(54) CARBON DIOXIDE ABSORBER FOR A REBREATHING SYSTEM

(71) Applicant: Dräger Medical GmbH, Lübeck (DE)

(72) Inventors: Ahmet Türker, Lübeck (DE); Grigory Kholtchanski, Lübeck (DE); Sven Pasdzior, Lübeck-Travemünde (DE); Robert Lischinski, Neubrandenburg (DE); Dirk-Stefan Reichert, Lübeck (DE)

(73) Assignee: Dräger Medical GmbH, Lübeck (DE)

(21) Appl. No.: 14/487,528

(22) Filed: Sep. 16, 2014

Related U.S. Patent Documents

Reissue of:
(64) Patent No.: 8,286,633
Issued: Oct. 16, 2012
Appl. No.: 12/129,911
Filed: May 30, 2008

(30) Foreign Application Priority Data

Jun. 2, 2007 (DE) ..... 10 2007 025 809

(51) Int. Cl.

| | |
|---|---|
| ***A63B 31/00*** | (2006.01) |
| ***A61M 16/22*** | (2006.01) |
| ***A62B 19/00*** | (2006.01) |
| ***A62B 9/04*** | (2006.01) |
| *B01D 53/04* | (2006.01) |

(52) U.S. Cl.
CPC ..... *A61M 16/22* (2013.01); *A62B 9/04* (2013.01); *A62B 19/00* (2013.01); *B01D 53/0446* (2013.01); *B01D 53/0415* (2013.01); *B01D 2257/504* (2013.01); *B01D 2259/4533* (2013.01); *Y02C 10/08* (2013.01)

(58) Field of Classification Search
USPC ..... 128/205.12, 205.28; 96/147; 55/504, 55/508
See application file for complete search history.

(56) References Cited

U.S. PATENT DOCUMENTS

| | | | | |
|---|---|---|---|---|
| 3,830,632 | A * | 8/1974 | Guzay | 422/120 |
| 4,266,539 | A * | 5/1981 | Parker et al. | 128/204.26 |
| 4,353,366 | A * | 10/1982 | Bickford | 128/205.12 |
| 4,841,953 | A * | 6/1989 | Dodrill | 128/202.27 |
| 4,991,576 | A * | 2/1991 | Henkin et al. | 128/203.28 |
| 5,002,050 | A * | 3/1991 | McGinnis | 128/204.18 |
| 5,452,713 | A * | 9/1995 | Vipond et al. | 128/204.18 |
| 5,744,030 | A * | 4/1998 | Reid et al. | 210/235 |
| 5,765,550 | A * | 6/1998 | Psaros et al. | 128/202.27 |
| 6,440,201 | B1 * | 8/2002 | Billiet | 96/147 |
| 6,461,397 | B1 * | 10/2002 | Billiet | 55/498 |
| 6,491,034 | B1 * | 12/2002 | Gunaratnam et al. | 128/204.18 |
| 6,581,598 | B1 * | 6/2003 | Foran et al. | 128/204.23 |
| 7,174,893 | B2 * | 2/2007 | Walker et al. | 128/206.21 |

(Continued)

FOREIGN PATENT DOCUMENTS

DE 102004020133 B3 8/2005

*Primary Examiner* — Cary Wehner
(74) *Attorney, Agent, or Firm* — Taft Stettinius & Hollister LLP

(57) ABSTRACT

A carbon dioxide absorber for a rebreathing system can be connected to a connection head of the rebreathing system in a simple manner. A centering device (43, 44, 45, 46), provided in the area of a guide plate (40) of the absorber (4), can be caused to mesh with centering pins pointing in the direction of the absorber from the connection head.

23 Claims, 10 Drawing Sheets

(56) References Cited

U.S. PATENT DOCUMENTS

| | | | | |
|---|---|---|---|---|
| 7,344,582 | B2 * | 3/2008 | Pearson et al. | 55/504 |
| 7,424,889 | B2 * | 9/2008 | Mashak | 128/205.28 |
| 7,442,220 | B2 * | 10/2008 | Pearson et al. | 55/418 |
| 7,487,776 | B2 * | 2/2009 | Kleinschmidt | 128/205.12 |
| 7,802,568 | B2 * | 9/2010 | Eicher et al. | 128/200.14 |
| 7,850,765 | B2 * | 12/2010 | Kleinschmidt | 96/147 |
| 7,964,024 | B2 * | 6/2011 | Chen et al. | 95/139 |
| 8,210,178 | B2 * | 7/2012 | Schermeier et al. | 128/205.28 |
| D701,316 | S * | 3/2014 | Buckley | D24/164 |
| 2005/0235994 | A1 * | 10/2005 | Kleinschmidt | 128/205.12 |
| 2007/0215159 | A1 * | 9/2007 | Ross et al. | 128/205.28 |
| 2009/0107505 | A1 * | 4/2009 | Kleinschmidt | 128/205.28 |
| 2009/0188505 | A1 * | 7/2009 | Smart et al. | 128/205.24 |
| 2011/0168180 | A1 * | 7/2011 | Lugtigheid | 128/205.14 |

* cited by examiner

CARBON DIOXIDE ABSORBER FOR A REBREATHING SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application claims the benefit of priority under 35 U.S.C. § 119 of German Patent Application DE 10 2007 025 809.9 filed Jun. 2, 2007, the entire contents of which are incorporated herein by reference.

FIELD OF THE INVENTION

The present invention pertains to a carbon dioxide absorber for a rebreathing system.

BACKGROUND OF THE INVENTION

A carbon dioxide absorber in the form of an absorber cartridge for a rebreathing system is known from DE 10 2004 020 133 B3. The carbon dioxide absorber is fastened to a connection head of the rebreathing system by means of a pivotable mount. The connection head is used to connect the absorber to the rebreathing system or to also replace a used absorber with a new one even during operation. Valves are provided for this within the connection head; on the one hand, these valves bridge over the gas ducts to the absorber in the form of a bypass when the absorber has been removed, so that no gas can escape from the rebreathing system. On the one hand, a gas connection is established to the absorber when the absorber is connected to the connection head. The absorber has, on its top side, a guide plate, which is pushed into the pivotable mount on the connection head. To center the absorber in relation to the connection head, a centering notch is provided at the guide plate and a centering pin on the mount. The absorber is connected to the connection head when the centering pin is in contact with the wedge-shaped centering notch. However, there always is a certain clearance between the pivotable mount and the connection head because of manufacturing tolerances, so that a mismatch may develop between the gas ducts of the connection head and of the absorber. Since the absorber is normally fastened to the underside of the rebreathing system, the centering notch and the centering pin are normally not visible to the user. Thus, the user cannot readily recognize whether the centering pin is located within the centering notch when the absorber is inserted into the mount in a tilted position.

SUMMARY OF THE INVENTION

The basic object of the present invention is to improve a carbon dioxide absorber such that it can be connected to the connection head of a rebreathing system in a simple manner.

According to the invention, a carbon dioxide absorber is provided for a rebreathing system. The carbon dioxide absorber comprises a connection head at the rebreathing system with the connection head including a pivotable mount. The absorber has an absorber housing with a guide plate on a front side of the absorber housing, the guide plate being able to be pushed into the pivotable mount of the connection head. Guide plate gas ducts are arranged concentrically at the guide plate. Connection head gas ducts are provided in the connection head and with a design corresponding to the guide plate gas ducts. The guide plate gas ducts are for connection to the connection head gas ducts. Guide grooves are provided between the guide plate and the absorber housing for connecting the guide plate to the mount. Centering pins point in the direction of the absorber housing from the connection head. A centering means is in one or more of the guide plate and the absorber housing. The centering means is for meshing with the centering pins from the connection head.

The centering means may comprise upper positioning grooves arranged opposite each other with corresponding centering pins in the area of the guide grooves. The centering means may further comprise lower positioning grooves at the absorber housing, the lower positioning grooves extending flush with the upper positioning grooves and for meshing with free ends of the centering pins. The centering pins may taper towards a free end thereof in a wedge-shaped pattern. An outer contour of the centering pins may correspond to an inner contour of the upper positioning grooves. An outer contour of the centering pins may correspond to an inner contour of the lower positioning grooves.

The advantage of the present invention is essentially that the absorber is centered in relation to the connection head by upper positioning grooves at the guide plate in combination with centering pins, which engage the upper positioning grooves from the connection head. Increased tightness of the gas ducts is achieved in the connection area between the absorber and the connection head due to the improved centering of the absorber in relation to the connection head.

In the absorber known from DE 10 2004 020 133 B3 (which corresponds to U.S. patent application Ser. No. 11/058,624 filed Feb. 15, 2005), the absorber is centered in relation to the pivotable mount only. A centering notch is provided for this purpose in the guide plate of the absorber, and a centering pin, which is located within the centering notch in the inserted state of the absorber, is located at the bracket. Provisions are made according to the present invention for the centering pins to be arranged directly at the connection head such that these mesh with lateral upper positioning grooves at the guide plate of the absorber when the mount is pivoted in the direction of the connection head. The absorber is thus directly centered in relation to the connection head. The upper positioning grooves are preferably arranged in the area of the lateral guide grooves of the absorber. However, other areas of the guide plate or of the absorber housing are also suitable for centering if they can be caused to mesh with the centering pin of the connection head when the mount is pivoted.

The centering pins are advantageously arranged opposite each other in the area of the guide grooves.

It is especially advantageous to additionally provide in the absorber housing lower positioning grooves, which extend flush with the upper positioning grooves and act as a stop for the centering pins. Centering is further improved by the lower positioning grooves, because the centering pins can be caused to mesh both with the upper and lower positioning grooves.

It is advantageous to make the centering pins wedge-shaped in such a way that they taper towards the free end, and to design, in addition, the upper positioning grooves and the lower positioning grooves corresponding thereto. The centering pins are thus in contact with the upper positioning grooves and the lower positioning grooves in a positive-locking manner in the coupled state of the absorber.

An exemplary embodiment of the present invention is shown in the figure and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

Figure 1:
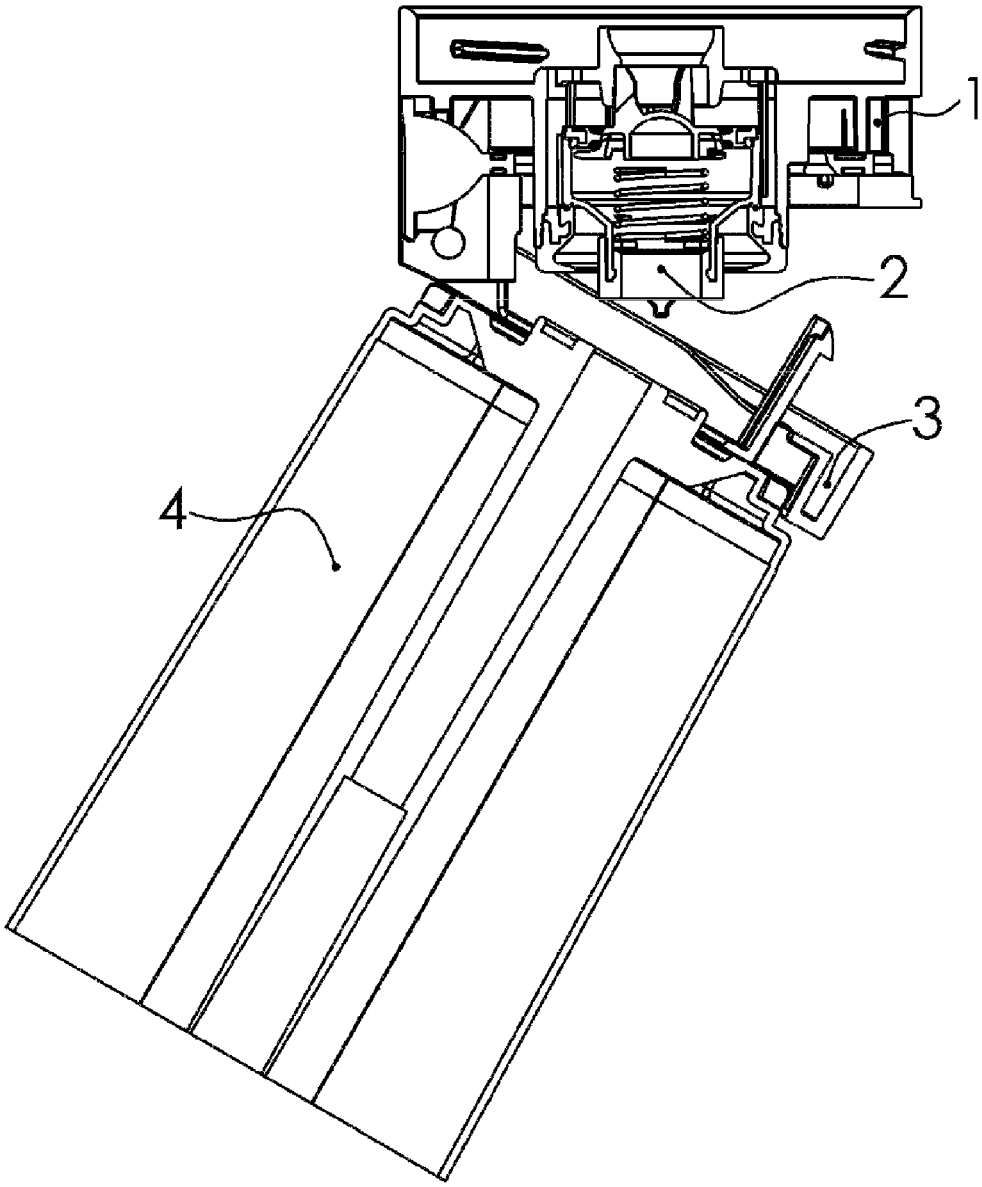
FIG. 1 is a sectional view showing a connection head with an absorber.

Referring to the drawings in particular, FIG. 1 schematically shows a longitudinal section of a connection head 1 with a valve means 2 and with an absorber 4 accommodated in a pivotable mount 3.

Figure 2:
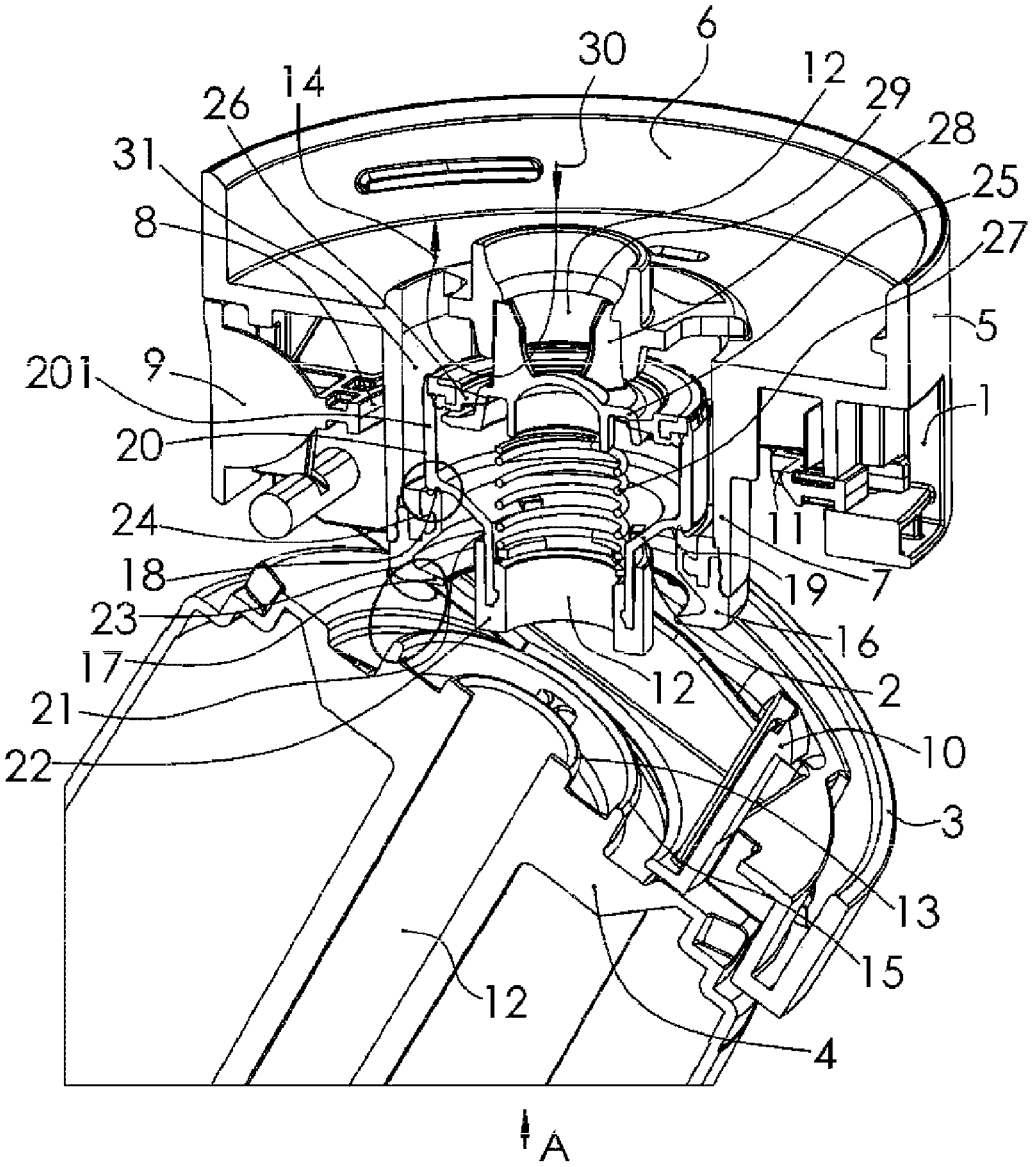
FIG. 2 is a schematic sectional perspective view showing a connection area between the connection head and the absorber according to FIG. 1.

FIG. 2 schematically illustrates the connection area between the connection head 1 and the absorber 4.

The connection head 1 has a housing 5 with a connection piece 6 for connection to an anesthetic breathing system, not shown more specifically in FIG. 2; a guide sleeve 7, which accommodates the valve means 2, and an annular locking element 8 within the housing 5 with a release button 9.

The mount 3, which receives the absorber 4, has a barb 10, which snaps into a wall section 11 of the locking element 8. To connect the absorber 4 to the connection head 1, the absorber 4 is pushed into the mount 3 and pivoted in the direction of the connection head 1. Reference is made in this connection to the disclosure of DE 10 2004 020 133 B3, which is part of this specification (and is incorporated by reference and corresponding U.S. patent application Ser. No. 11/058,624 filed Feb. 15, 2005, is also hereby incorporated by reference.

The absorber 4 has an inner gas duct 12 with an inner valve crater 13 and an outer gas duct 14 arranged concentrically thereto with an outer valve crater 15. The gas ducts 12, 14 describe the flow paths through the absorber 4.

The inner gas duct 12 passes within the connection head 1 through the interior space of the valve means 2, and the outer gas duct 14 in an annular space between the valve means 2 and the guide sleeve 7. A sealing ring 16, which has an outer sealing lip 17 directed towards the absorber 4, and an inner sealing lip 18, which is in contact with an outer ring section 19 of the valve means 2, is located on the underside of the guide sleeve 7. The ring section 19 is located between a first cylindrical wall section 20 of the valve means 2 with the larger cross section and a second cylindrical wall section 21 with a smaller diameter, which latter wall section adjoins same. The wall sections 20, 21 and the ring section 19 together form a valve housing 201 of the valve means 2. The inner sealing lip 18 and the ring section 19 form a second sealing area 24 and are designed to interrupt the gas flow in the annular space as a shut-off means when the absorber 4 has been removed from the connection head 1.

The second wall section 21 is provided with an elastomer ring 22 at its free end, which extends in the direction of the absorber 4. When the absorber 4 is pivoted in the direction of the connection head 1, the outer sealing lip 17 lies on the outer valve crater (seat) 15 and forms a first sealing area 23. The elastomer ring 22 is located on the inner valve crater 13 in this position of the absorber 4.

A flow valve 31 with a valve body 25, which is in contact with a sealing lip 26, is located on the top side of the first wall section 20 of the valve means 2. The valve body 25 is pressed by a compression spring 27 against the sealing lip 26. The valve body 25 is in contact with a projection 29 of the housing 5 via spacers 28. Due to the fixation by means of the spacers 28, the valve body 25 always has a fixed position in relation to the housing 5. The flow valve 31 opens when the valve housing 201 is displaced in the direction of the spacers 28. In the position of the absorber 4 shown in FIG. 2, the path of gas 30 extends via the inner gas duct 12 through the free spaces between the spaces 28 to the outer gas duct 14.

Figure 3:
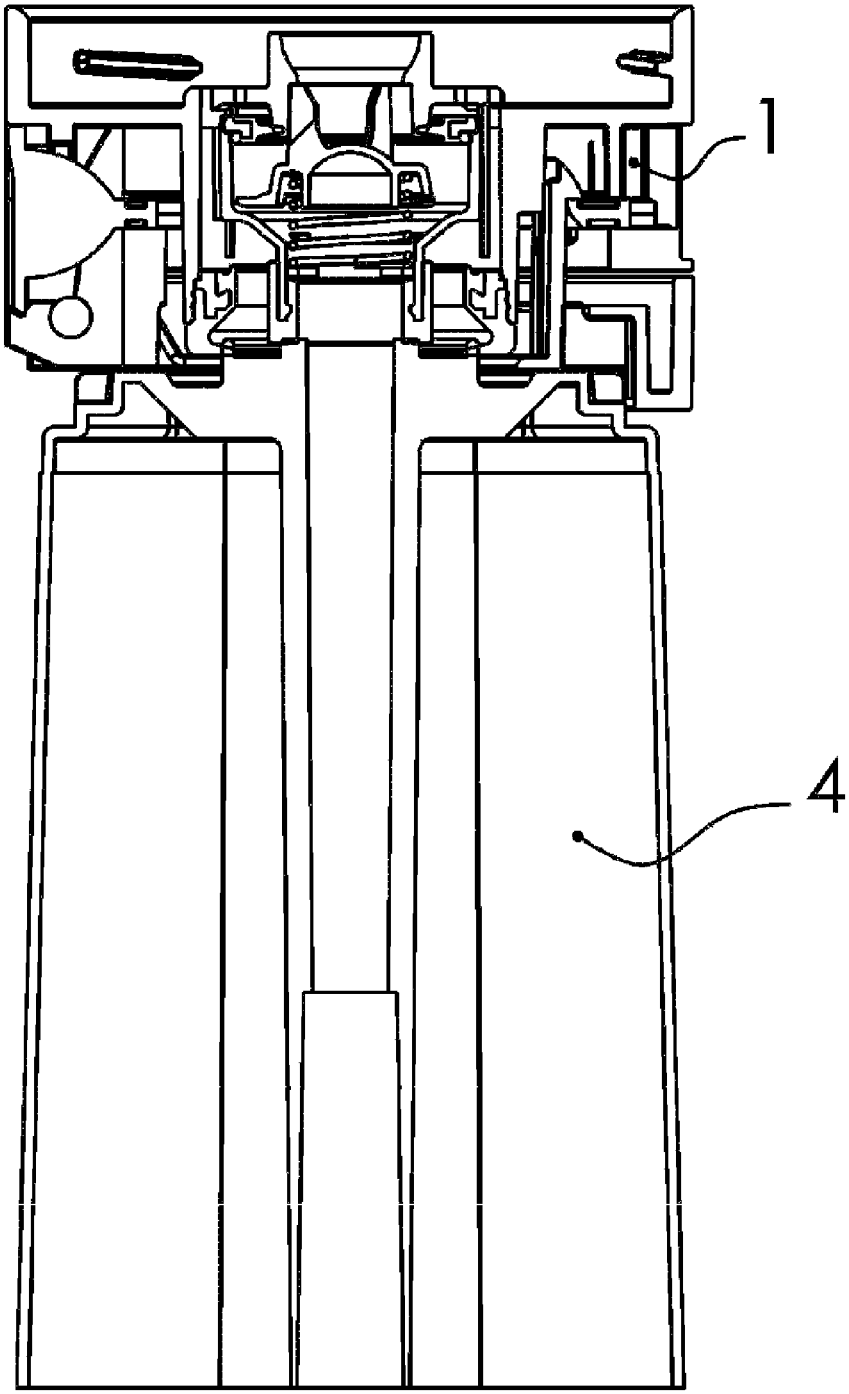
FIG. 3 is a sectional view showing an absorber connected to the connection head.

FIG. 3 shows the connection head 1 with the connected absorber 4.

Figure 4:
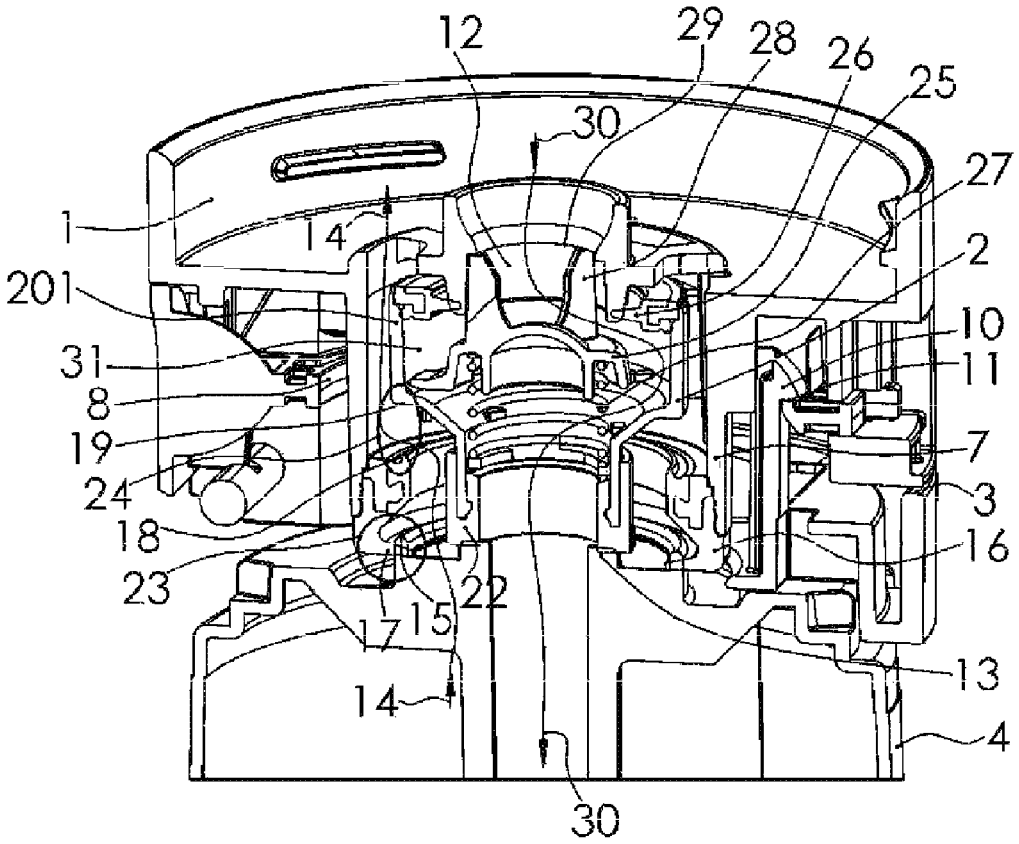
FIG. 4 is sectional perspective view showing the connection area in a longitudinal section between the connection head and the absorber according to FIG. 3.

FIG. 4 shows the connection area between the connection head 1 and the absorber 4 corresponding to FIG. 3 in a longitudinal section. Identical components are designated by the same reference numbers as in FIGS. 1 and 2. The barb 10 has snapped into the wall section 11 of the spring element 8 in the coupled state. The outer valve crater 15 is in contact with the outer sealing lip 17. The inner valve crater 13 is located at the elastomer ring 22 and presses the valve housing 201 of the valve means 2 upward against the force of the compression spring 27. Since the valve body 25 is supported at the projection 29 via the spacers 28 and thus remains in its original position, the sealing lip 26 lifts off from the valve body 25 and the flow valve 31 is opened. At the same time, the ring section 19 separates from the inner sealing lip 18 and the second sealing area 24 is opened. The path of gas 30 from the anesthetic breathing system now leads via the opened flow valve 31 in the inner gas duct 12 and to the absorber 4. The backflow takes place via the outer gas duct 14, the opened second sealing area 24 and the annular gap between the valve means 2 and the guide sleeve 7 back to the anesthetic breathing system.

The outer sealing lip 17 is designed in this embodiment as a lip seal with a large deformation area in order to reduce the sealing forces that must be overcome when the mount 3 is coupled with the connection head 1 and to compensate differences in height in the form of manufacturing tolerances.

With the absorbed 4 uncoupled, the sealing ring 16 is pulled off from the guide sleeve 7 downward for cleaning purposes and the valve means 2 can be removed and taken apart for cleaning purposes. No tool is necessary for disassembly. The components of the connection head 1 may be manufactured from plastic according to the injection molding process and can be manufactured at a very low cost as a result.

Figure 5:
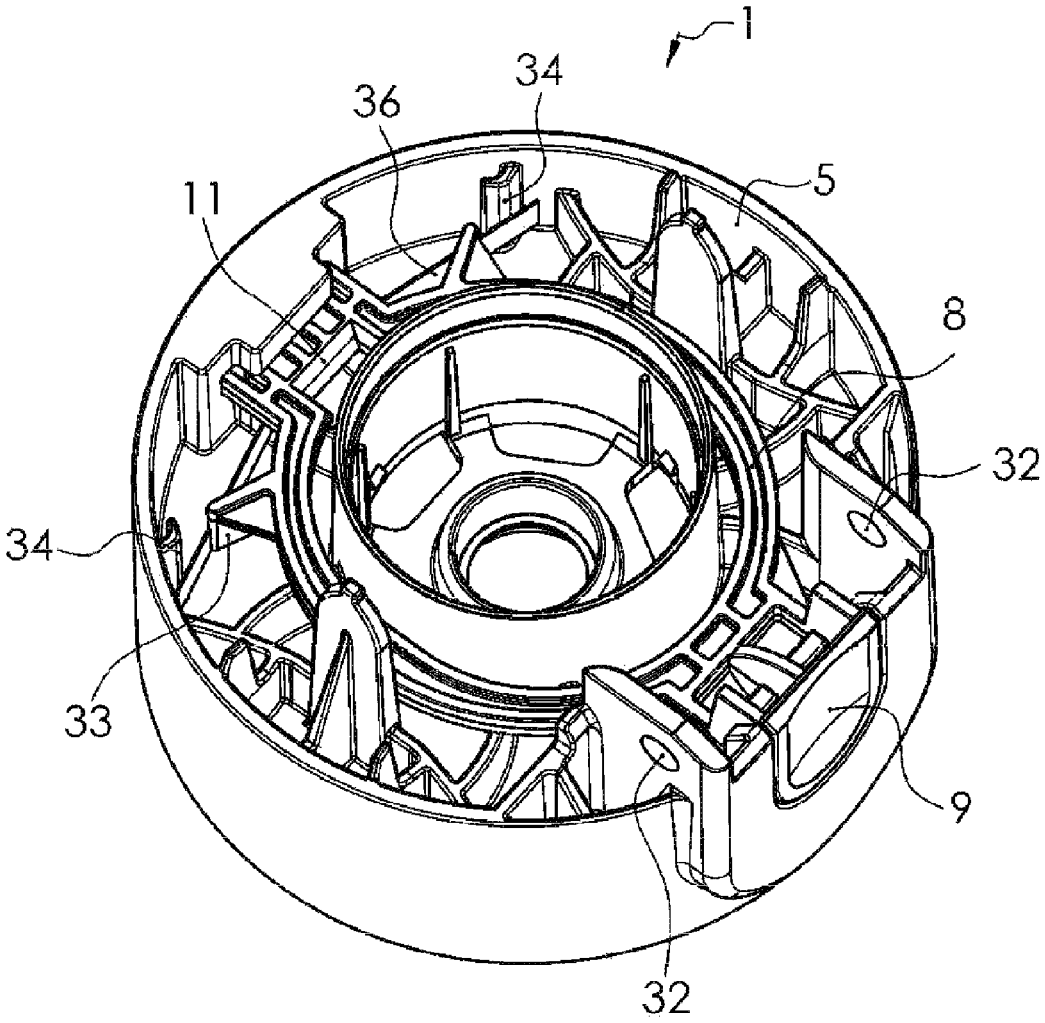
FIG. 5 is a perspective view of the underside of the connection head with the locking element inserted.

FIG. 5 shows a bottom view of the connection head 1 with the valve means 2 removed and with the bracket 3 removed in view "A" according to FIG. 2. The mount 3 is fastened pivotably in the bushes 32 of the housing 5. The locking element 8 has spacing elements 33, which are in contact with a leaf spring 36, the leaf spring 36 being supported at projections 34 of the housing 5.

Figure 6:
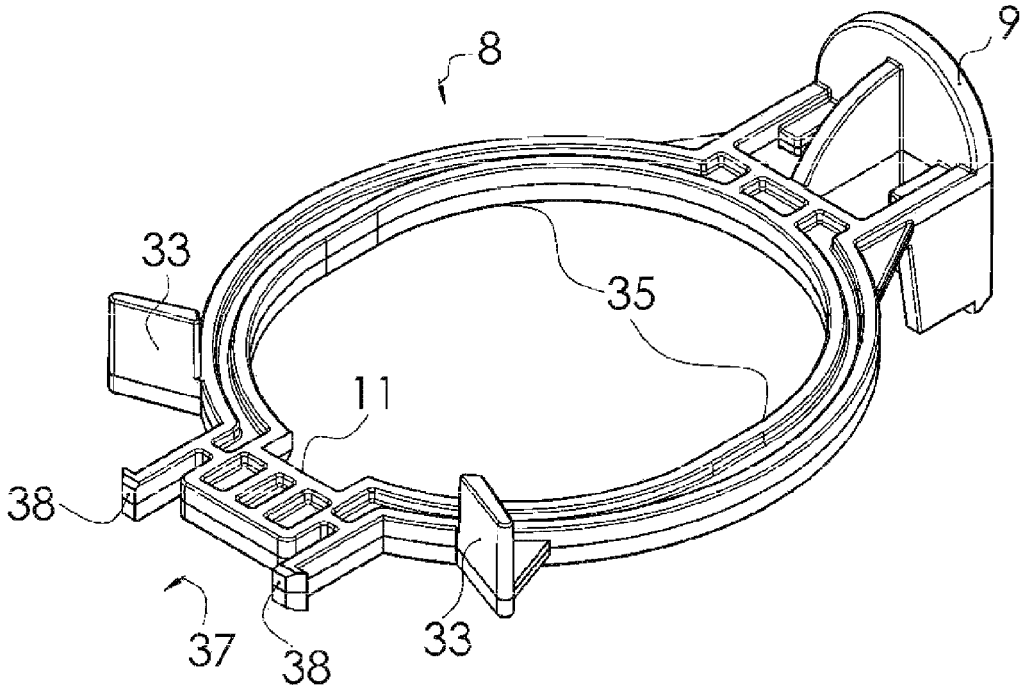
FIG. 6 is a perspective view of the locking element according to FIG. 5.

FIG. 6 shows the locking element 8 in a perspective view. The locking element 8 comprises a rigid frame 35, to which the likewise rigid spacing elements 33 are fastened. When pressure is applied to the release button 9, the frame 35 deforms and the wall section 11 is displaced in the direction of arrow 37 against the spring force of the leaf spring 36, FIG. 5. The stroke of the locking element 8 is limited by a contact surface 38, which is in contact with the housing 5, FIG. 5, at maximum deflection. When pressure is applied to the release button 9, the barb 10, FIG. 2, is released.

Figure 7:
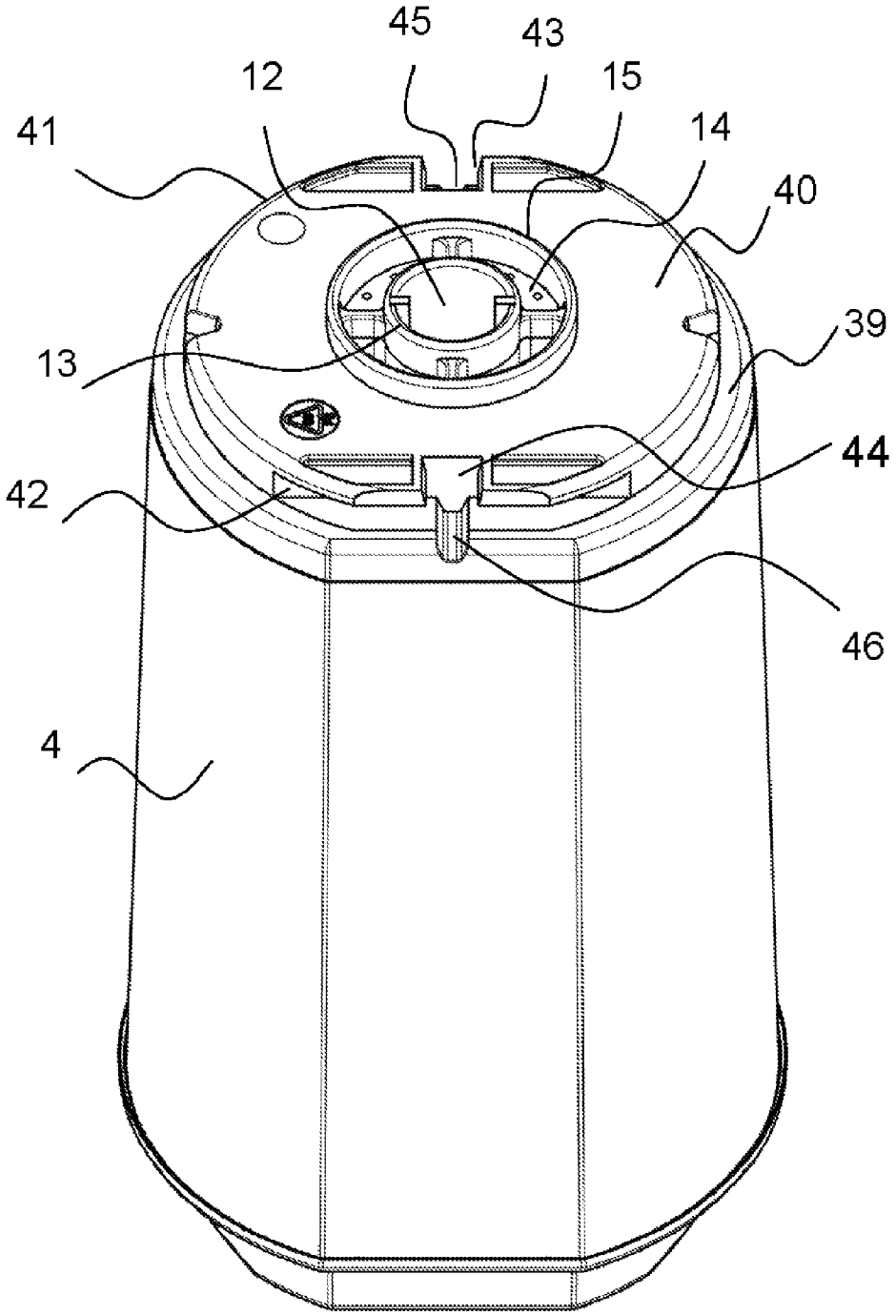
FIG. 7 is a perspective view showing the absorber according to FIG. 1.

FIG. 7 illustrates the absorber 4 in a perspective view. A guide plate 40 is fastened to the top side of an absorber housing 39, and guide grooves 41, 42 arranged opposite each other are provided between the guide plate 40 and the absorber housing 30. The guide plate 40 has upper positioning grooves 43, 44 arranged opposite each other in the area of the guide grooves 41, 42 and lower positioning grooves 45, 46 extending flush with the upper positioning grooves 43, 44.

Figure 8:
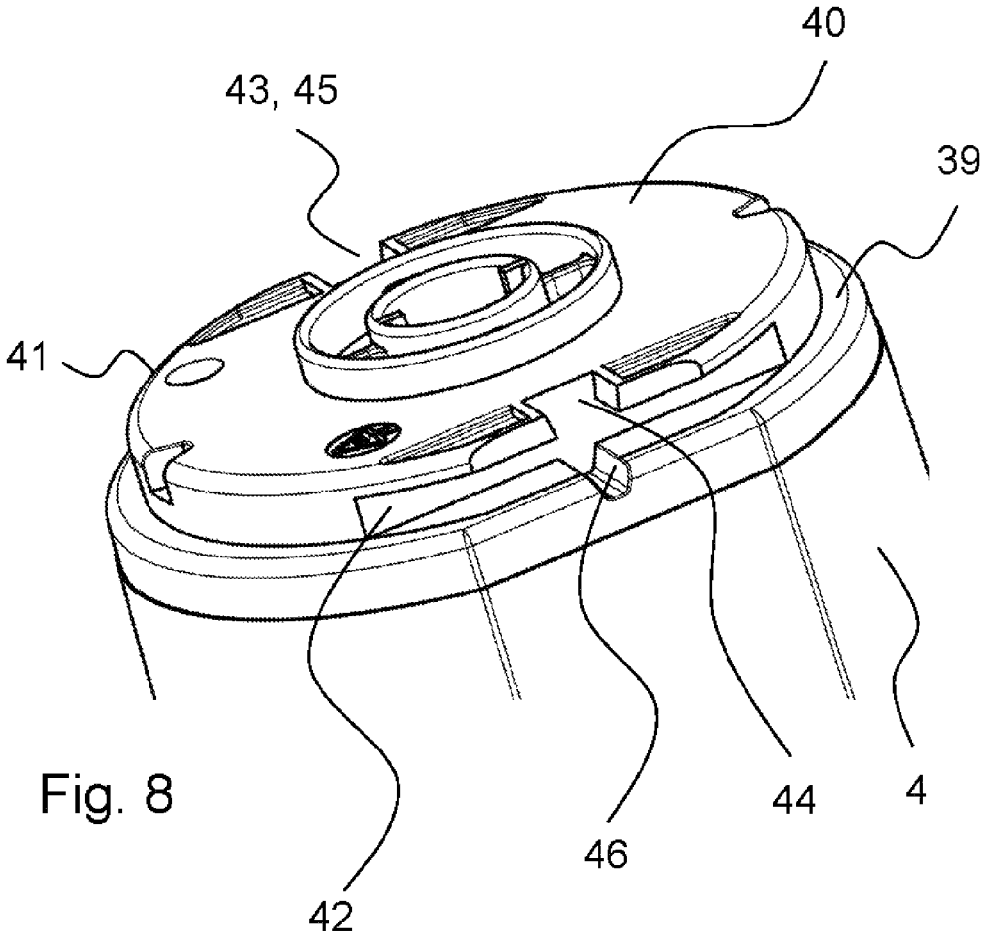
FIG. 8 is a perspective view showing the absorber according to FIG. 7 in the area of the guide plate.

FIG. 8 shows the absorber 4 in the area of the guide plate 40 in a perspective view. Identical components are designated by the same reference numbers as in FIG. 7.

Figure 9:
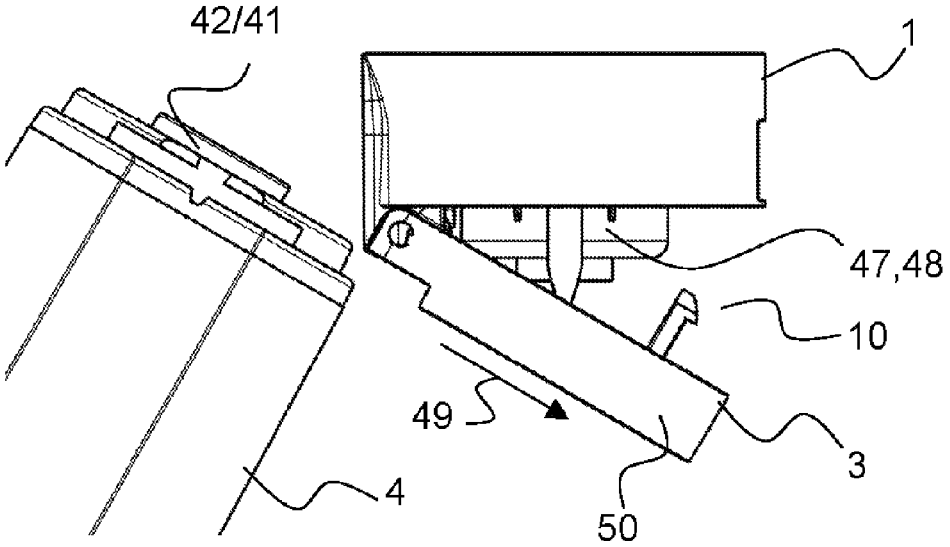
FIG. 9 is a side broken away view showing the absorber before insertion into the mount.

FIG. 9 shows the absorber 4 before insertion into the mount 3 of the connection head 1. The connection head 1 has centering pins 47, 48, which are arranged opposite each other and of which only the front centering pin 47 is shown in FIG. 9. The centering pins 47, 48 are designed as pins tapering in a wedge-shaped manner towards the free end. To connect the absorber 4 to the mount 3, the absorber is pushed into the underside 50 of the mount 3 along arrow 49. The underside 50 is beveled for this inwardly, so that the guide plate 40 is held by the underside 50. The guide grooves 41, 42 extend in the area of the centering pins 47, 48.

Figure 10:
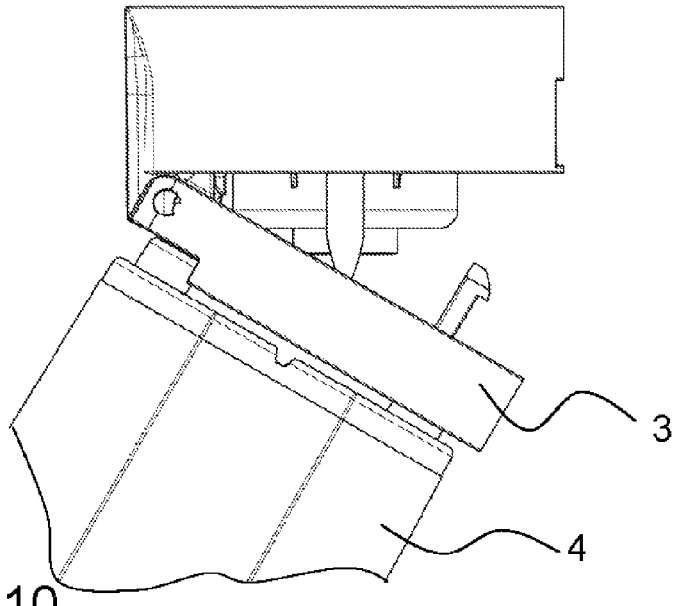
FIG. 10 is a side broken away view showing the mount with the absorber inserted.

FIG. 10 shows the mount 3 with the absorber 4 pushed in.

Figure 11:
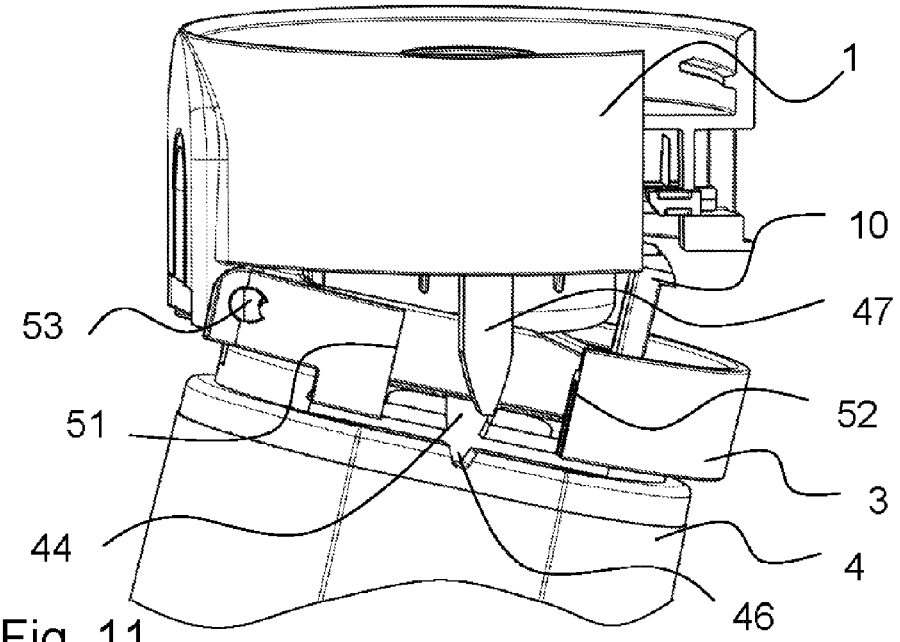
FIG. 11 is a perspective broken away view showing the mount with the absorber in a sectional view.

FIG. 11 shows the mount 3 with the absorber 4 inserted, the mount being cut open along the section lines 51, 52. The centering pin 47 is located in the area of the upper positioning groove 44 of the guide plate 40. Identical components are designated by the same reference numbers as in FIGS. 8 and 9. The mount 3 is fastened such that it can be pivoted about a pin joint *53* fastened to the connection head 1.

Figure 12:
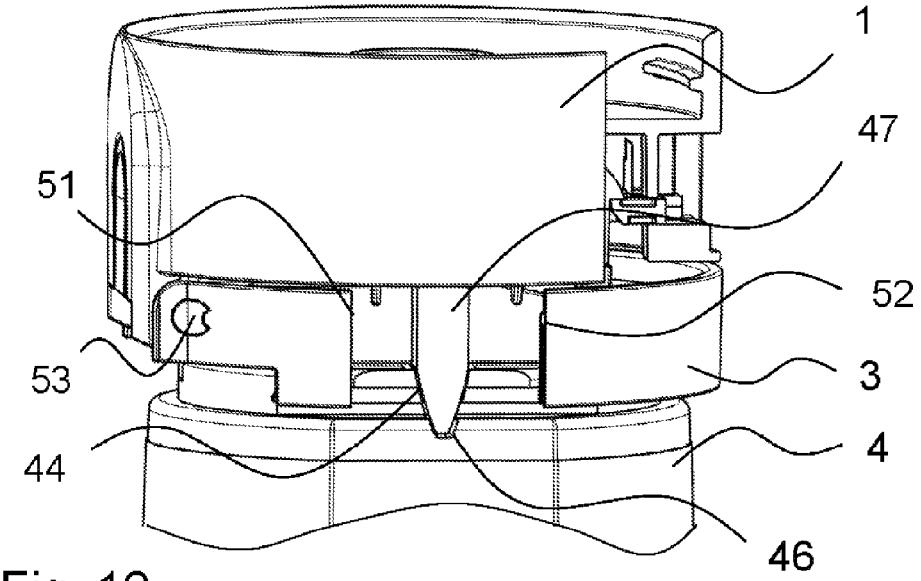
FIG. 12 is a side broken away view showing the mount according to FIG. 11 with the mount snapped into the connection head.

FIG. 12 shows the mount 3 connected to the connection head 1. The front centering pin 47 is located completely within the upper positioning groove 44 and lies with its tip within the lower positioning groove 46. The rear centering pin 48, not shown in FIG. 12, is located within the rear upper positioning groove 43 and lies with its tip within the lower positioning groove 45. The free ends of the centering pins 47, 48 taper in a wedge-shaped manner, and the inner walls of the upper positioning grooves 43, 44 and of the lower positioning grooves 45, 46 are designed corresponding thereto, so that the absorber 4 has only a very small clearance in relation to the connection head 1.

While a specific embodiment of the invention has been shown and described in detail to illustrate the application of the principles of the invention, it will be understood that the invention may be embodied otherwise without departing from such principles.

What is claimed is:

1. A carbon dioxide absorber for a rebreathing system, the carbon dioxide absorber comprising:

a connection head at the rebreathing system, said connection head including a pivotable mount;

an absorber housing;

a guide plate on a front side of said absorber housing, said guide plate being pushed into said pivotable mount of said connection head;

guide plate gas ducts arranged concentrically at said guide plate;

connection head gas ducts provided in said connection head and with a design corresponding to said guide plate gas ducts, said guide plate gas ducts for connection to said connection head gas ducts;

guide grooves between said guide plate and said absorber housing for connecting said guide plate to said mount;

centering pins pointing in a direction of said absorber housing from said connection head; and centering means in one or more of said guide plate and said absorber housing, said centering means for meshing with said centering pins from said connection head;

said pivotable mount being pivotable between a first position and a second position, said first position arranging said pivotable mount adjacent said connection head, said second position arranging said pivotable mount spaced from said connection head and said centering pins.

2. A carbon dioxide absorber in accordance with claim 1, wherein said centering means comprises upper positioning grooves arranged opposite each other with corresponding said centering pins in an area of said guide grooves.

3. A carbon dioxide absorber in accordance with claim 2, wherein said centering means further comprises lower positioning grooves at said absorber housing, said lower positioning grooves extending flush with said upper positioning grooves and for meshing with free ends of said centering pins.

4. A carbon dioxide absorber in accordance with claim 1, wherein said centering pins taper towards a free end thereof in a wedge-shaped pattern.

5. A carbon dioxide absorber in accordance with claim 4, wherein:

said centering means comprises upper positioning grooves arranged opposite each other with corresponding said centering pins in an area of said guide grooves; and an outer contour of said centering pins corresponds to an inner contour of said upper positioning grooves.

6. A carbon dioxide absorber in accordance with claim 4, wherein:

said centering means comprises lower positioning grooves at said absorber housing, said lower positioning grooves for meshing with free ends of said centering pins; and an outer contour of said centering pins corresponds to an inner contour of said lower positioning grooves.

7. A carbon dioxide absorber in accordance with claim 1, wherein:

said pivotable mount defines an opening;

said centering means defines positioning grooves as part of said centering means, said centering pins passing through said opening of said pivotable mount, and into said positioning grooves of said centering means when said pivotable mount moves from said first position into said second position.

8. A rebreathing system with carbon dioxide absorber comprising:

a rebreathing system connection head including a pivotable mount, said connection head having connection head gas ducts provided in said connection head, said connection head having centering pins pointing outwardly from said connection head;

an absorber housing with a guide plate on a front side of said absorber housing, said guide plate for being pushed into said pivotable mount of said connection head, said guide plate including guide plate gas ducts arranged concentrically at said guide plate with a design corresponding to said connection head gas ducts, said connection head gas ducts for connection to said guide plate gas ducts, guide grooves being provided between said guide plate and said absorber housing for connecting said guide plate to said mount; and centering means in one or more of said guide plate and said absorber housing, said centering means for meshing with said centering pins from said connection head, said centering means defining upper positioning grooves arranged opposite each other with corresponding said centering pins in an area of said guide grooves, said centering means further defining lower positioning grooves at said absorber housing, said lower positioning grooves extending flush with said upper positioning grooves and for meshing with free ends of said centering pins.

9. A rebreathing system with carbon dioxide absorber in accordance with claim 8, wherein said centering pins taper towards a free end thereof in a wedge-shaped pattern.

10. A rebreathing system with carbon dioxide absorber in accordance with claim 9, wherein:

an outer contour of said centering pins corresponds to an inner contour of said upper positioning grooves.

11. A rebreathing system with carbon dioxide absorber in accordance with claim 9, wherein:

an outer contour of said centering pins corresponds to an inner contour of said lower positioning grooves.

12. A carbon dioxide absorber arrangement in a rebreathing system, the absorber arrangement comprising:

an absorber housing for holding a carbon dioxide absorber material, said absorber housing defining ducts for bringing breathing gas in contact with the carbon dioxide absorber material;

a guide plate mounted on one side of said absorber housing, one of said guide plate and said absorber housing defining a positioning groove;

a pivotable mount adapted to connect to said guide plate, said pivotable mount and said guide plate being shaped to have said guide plate slide into said pivotable mount in a direction along said one side of said absorber housing;

a connection head adapted to connect to the rebreathing system and defining connection head ducts in communication with the rebreathing system, said pivotable mount being pivotally connected to said connection head to bring said ducts of said absorber housing into communication with said ducts of said connection head;

a centering pin extending from said connection head in a direction of said absorber housing, said centering pin cooperating with said positioning groove to align said ducts of said absorber housing with said ducts of said connection head;

said pivotable mount being pivotable between a first position and a second position, said first position arranging said ducts of said absorber housing in communication with said ducts of said connection head, said second position arranging said pivotable mount spaced from said connection head and said centering pin.

13. An absorber arrangement in accordance with claim 12, wherein:

said pivotable mount defines an opening, said centering pin passing through said opening, and into said positioning groove when said pivotable mount moves from said first position into said second position.

*14. A carbon dioxide absorber cartridge for a rebreathing system, the carbon dioxide absorber cartridge comprising:*

*an absorber housing, the absorber housing being configured to connect with a pivotable mount of a connection head of a rebreathing system;*

*a guide plate provided as a front side of the absorber housing, the guide plate being configured for insertion into the pivotable mount of the connection head;*

*guide plate gas ducts arranged concentrically at the guide plate, and configured to correspond to and connect with gas ducts in the connection head;*

*guide grooves defined by at least one of the guide plate and a portion of the absorber housing for connecting the guide plate to the mount, the guide grooves arranged opposite each other on lateral sides of the guide plate and substantially parallel to a direction of insertion into the connection head;*

*upper positioning grooves arranged opposite each other on lateral sides of the guide plate and in an area of the guide grooves, and substantially along a line perpendicular to the direction of insertion and bisecting the concentrically arranged gas ducts, the upper positioning grooves being configured to mesh with centering pins extending from the connection head which point in a direction of the absorber housing when the absorber is inserted into the pivotable mount and the mount is pivoted from a second position arranging the pivotable mount spaced from the connection head and the centering pins to a first position arranging the pivotable mount adjacent the connection head.*

*15. A carbon dioxide absorber cartridge for a rebreathing system in accordance with claim 14, wherein the upper positioning grooves are arranged opposite each other for meshing with free ends of the centering pins.*

*16. A carbon dioxide absorber cartridge for a rebreathing system in accordance with claim 15, further comprising lower positioning grooves at the absorber housing, the lower positioning grooves extending in alignment with the upper positioning grooves and for at least one of meshing with free ends of the centering pins and providing clearance for free ends of the centering pins.*

*17. A carbon dioxide absorber cartridge for a rebreathing system in accordance with claim 14, wherein:*

*side walls of the positioning grooves slant inwards towards each other in a direction from top to bottom such that the side walls are configured to guide and engage with the centering pins that have a taper in a wedge shaped pattern.*

*18. A carbon dioxide absorber cartridge for a rebreathing system in accordance with claim 14, wherein the guide grooves are substantially identical with each other.*

*19. An absorber for a rebreathing system, the absorber comprising:*

*an absorber housing first side;*

*a plurality of gas ducts arranged in said first side, one gas duct of said plurality of gas ducts being arranged concentrically around a gas duct axis, another of said plurality of gas ducts being arranged adjacent said one gas duct;*

*an absorber housing second side extending away from said first side in a direction of said gas duct axis;*

*first and second guide grooves arranged in said second side, each of said first and second guide grooves having a longitudinal axis, said longitudinal axes being arranged parallel to each other and extending in an insertion direction, said first and second guide grooves being arranged on diametrically opposite sides of said plurality of gas ducts, said first and second guide grooves being adapted to insert the absorber into a mount of the rebreathing system in said insertion direction, said first and second guide grooves being adapted to fix said absorber with respect to the mount of the rebreathing system in directions perpendicular to said insertion direction;*

*first and second positioning openings arranged in said first side on diametrically opposite sides of said plurality of gas ducts, each of the first and second positioning openings being delimited by stop surfaces on diametrically opposite sides of each of said first and second openings with respect to said insertion direction, said stop surfaces being adapted to fix the absorber both forward and backward in said insertion direction with respect to a connection head of the rebreathing system, wherein said first and second guide grooves, and said first and second positioning openings are arranged to align said plurality of gas ducts of the absorber with gas ducts of the connection head.*

*20. An absorber in accordance with claim 19, wherein:*

*the absorber has a positioning axis perpendicular to said gas duct axis and said insertion direction, said stop surfaces of said positioning openings being arranged symmetrical with respect to said positioning axis whereby correct alignment of said stop surfaces and said gas ducts of the absorber is easily provided without having to determine offsets.*

*21. An absorber in accordance with claim 20, wherein:*

*said first and second positioning openings are arranged at an intersection of said first and second sides and are open on said second side whereby less material is needed to form the position openings and the positioning openings are easier to form.*

*22. An absorber in accordance with claim 20, wherein:*

*said first and second openings are each adapted to receive a pin of the connection head.*

*23. An absorber in accordance with claim 20, wherein:*

*said plurality of gas ducts are arranged concentrically around said gas duct axis;*

*said stop surfaces have a taper whereby said stop surfaces contact a pin of the connection head to guide the gas ducts of the absorber into proper alignment with the gas ducts of the connection head;*

*each of said guide grooves is defined by an upper wall and a lower wall;*

*each of said first and second positioning openings extend though said upper wall and the lower wall of one of said first and second guide grooves;*

*said first and second side define a centering notch at a forward or rear edge of the absorber in said insertion direction, whereby said centering notch is adapted to cooperate with a centering pin of a different connection head and limit movement of the absorber in said insertion direction and allow the absorber to be used with two different types of connection heads.*

* * * * *